United States Patent
Moreau et al.

(10) Patent No.: US 10,793,909 B2
(45) Date of Patent: Oct. 6, 2020

(54) METHODS FOR PREDICTING THE SURVIVAL TIME OF PATIENTS WITH DECOMPENSATED ALCOHOLIC CIRRHOSIS

(71) Applicants: INSERM (INSTITUT NATIONAL DE LA SANTE ET DE LA RECHERCHE MEDICALE), Paris (FR); UNIVERSITE PARIS DESCARTES, Paris (FR); ASSISTANCE PUBLIQUE-HOPITAUX DE PARIS (APHP), Paris (FR); UNIVERSITE PARIS DIDEROT—PARIS 7, Paris (FR)

(72) Inventors: Richard Moreau, Paris (FR); Emmanuel Weiss, Paris (FR); Pierre-Emmanuel Rautou, Paris (FR)

(73) Assignees: INSERM (INSTITUT NATIONAL DE LA SANTE ET DE LA RECHERCHE MEDICALE), Paris (FR); UNIVERSITE PARIS DESCARTES, Paris (FR); ASSISTANCE PUBLIQUE—HOPITAUX DE PARIS (APHP), Paris (FR); UNIVERSITE PARIS DIDEROT—PARIS 7, Paris (FR)

( * ) Notice: Subject to any disclaimer, the term of this patent is extended or adjusted under 35 U.S.C. 154(b) by 110 days.

(21) Appl. No.: 15/775,092

(22) PCT Filed: Nov. 9, 2016

(86) PCT No.: PCT/EP2016/077129
§ 371 (c)(1),
(2) Date: May 10, 2018

(87) PCT Pub. No.: WO2017/081073
PCT Pub. Date: May 18, 2017

(65) Prior Publication Data
US 2018/0320232 A1    Nov. 8, 2018

(30) Foreign Application Priority Data
Nov. 10, 2015    (EP) .................................. 15306785

(51) Int. Cl.
*C12Q 1/6883*    (2018.01)

(52) U.S. Cl.
CPC ...... *C12Q 1/6883* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

2001/0051344 A1* 12/2001 Shalon .................. B01L 3/0244
435/6.11

FOREIGN PATENT DOCUMENTS

JP    2010 502979 A    1/2010

OTHER PUBLICATIONS

Chan (Integrating Transcriptomic and Proteomics, 2006, pp. 1-4).*
Cheung et al (Cold Spring Harbor Symposia on Quantitative Biology, 2003, vol. LXVIII, pp. 403-407).*
Slonin, Nature Genetics Supplement, vol. 32, Dec. 2002, pp. 502-508.*
Baker. Journal of the National Cancer Institute, vol. 95, No. 7, Apr. 2, 2003.*
Emmanuel Weiss Magali Fasseu et al: "Expression microarray reveals an extensive defect in the interferon (IFN)—independent activation of antiviral genes in patients with alcoholic cirrhosis", Hepatology, vol. 58, No. S1, pp. 848A-849A, Oct. 1, 2013.
Mikhael Giabicani: "Gene-specific control of inflammation during lipopolysaccharide tolerance is altered in immune cells from patients with advanced cirrhosis", pp. 1-2, Nov. 4, 2014.

* cited by examiner

*Primary Examiner* — Sarae L Bausch
(74) *Attorney, Agent, or Firm* — W&C IP (57) ABSTRACT

The present invention relates to methods for predicting the survival time of patients with decompensated alcoholic cirrhosis. In particular, the present invention relates to a method for predicting the survival time of a patient with decompensated alcoholic cirrhosis comprising i) determining the expression level of OAS2 or MX2 in a sample of peripheral blood mononuclear cells obtained from the patient, ii) comparing the level determined at step i) with a predetermined reference value and iii) and concluding that the patient will have a short survival time when the level determined at step i) is higher than its predetermined reference value or concluding that the patient will have a long survival time when the level determined at step i) is lower than the predetermined reference value.

7 Claims, 1 Drawing Sheet

METHODS FOR PREDICTING THE SURVIVAL TIME OF PATIENTS WITH DECOMPENSATED ALCOHOLIC CIRRHOSIS

FIELD OF THE INVENTION

The present invention relates to methods for predicting the survival time of patients with decompensated alcoholic cirrhosis.

BACKGROUND OF THE INVENTION

Cirrhosis is a chronic disease of the liver whose prevalence will dramatically increase during the next decade. Cirrhosis can result from a number of chronic liver diseases such as alcoholic liver disease, chronic viral hepatitis, non-alcoholic steatohepatitis, autoimmune diseases of the liver (primary biliary cirrhosis, primary sclerosing cholangitis, and autoimmune hepatitis). Cirrhosis progresses over several years. The occurrence of complications indicates the transition to the phase called "decompensated" (approximately 100,000 patients per year in France); These complications include ascites (30 000 patients per year in France), gastrointestinal bleeding (10,000 episodes/year in France), renal failure and bacterial infections which is very common and often due to the translocation of Gram-negative intestinal bacteria. Mortality in cirrhosis is thus usually a consequence of decompensation or its ensuing complications. The treatment of choice for decompensated cirrhosis is liver transplantation and many such patients are placed on transplant waiting lists. Therefore predicting the survival time of patients with decompensated alcoholic cirrhosis is highly desirable for determining whether the patient shall be eligible to transplantation. The MELD (Model for End Stage Liver Disease) score is currently used for organ allocation. Although the MELD score predicts 90-day mortality based on bilirubin, INR (international normalized ratio) and serum creatinine, the predisposing factors for death and final events leading to mortality need to be improved.

SUMMARY OF THE INVENTION

The present invention relates to methods for predicting the survival time of patients with decompensated alcoholic cirrhosis. In particular, the present invention is defined by the claims.

DETAILED DESCRIPTION OF THE INVENTION

Although systemic inflammation is believed to be a major driver of mortality in patients with decompensated alcoholic cirrhosis, its mechanisms are unclear. On the basis of the results of microarray gene expression profiling performed in cirrhotic and healthy immune cells, the inventors hypothesized that baseline expression levels of genes involved in cell-autonomous immunity (most of which are type 1 IFN-inducible) and/or of genes encoding secreted inflammatory cytokines or chemokines by circulating mononuclear cells in patients with cirrhosis may be related to patient outcome. Thus, they measured the baseline gene expression in peripheral blood mononuclear cells (PBMCs) from patients with decompensated alcoholic cirrhosis and investigated their relationship with the risk of death. The inventors demonstrate that in PBMCs from patients with decompensated alcoholic cirrhosis, higher baseline levels of type 1 IFN-inducible genes involved in cell-autonomous immunity, but not expression of genes encoding secreted inflammatory cytokines/chemokines, are highly predictive of the risk of death. Deregulation of type 1 IFN-inducible gene expression in circulating immune cells may play a role in the mechanisms resulting in death from cirrhosis. More particularly, in univariate analysis, a higher MELD score, higher baseline expression of 8 IFN-inducible genes as well as higher IFN score values were significant predictors of death. In bivariate analysis including the IFN and MELD scores, only the former significantly predicted death (RR=3.58; 95% CI, 1.18-10.91; P=0.02). These results were mainly due to the elevated intrinsic prognostic value of OAS2 (RR=2.49; P=0.04) and MX2 (RR=1.35; P=0.01).

Accordingly a first object of the present invention relates to a method for predicting the survival time of a patient with decompensated alcoholic cirrhosis comprising i) determining the expression level of OAS2 or MX2 in a sample of peripheral blood mononuclear cells obtained from the patient, ii) comparing the level determined at step i) with a predetermined reference value and iii) and concluding that the patient will have a short survival time when the level determined at step i) is higher than its predetermined reference value or concluding that the patient will have a long survival time when the level determined at step i) is lower than the predetermined reference value.

As used herein the expression "decompensated alcoholic cirrhosis" has its general meaning in the art. In cirrhosis, the presence of jaundice, ascites, portal hypertensive gastrointestinal bleeding, and/or, hepatic encephalopathy, or any combination of these is considered decompensation. The above manifestations appear when the disease process overwhelms the compensatory mechanisms, either by disease progression or a superimposed acute insult.

The method is particularly suitable for predicting the duration of the overall survival (OS) of the patient. Those of skill in the art will recognize that OS survival time is generally based on and expressed as the percentage of people who survive for a specific amount of time. As used herein, the expression "short survival time" indicates that the patient will have a survival time that will be lower than the median (or mean) observed in the general population of patient with decompensated alcoholic cirrhosis. When the patient will have a short survival time, it is meant that the patient will have a "poor prognosis" and is at high risk of death on liver transplant waiting list. Inversely, the expression "long survival time" indicates that the patient will have a survival time that will be higher than the median (or mean) observed in the general population of patient with decompensated alcoholic cirrhosis and that he may survive until liver transplantation. When the patient will have a long survival time, it is meant that the patient will have a "good prognosis".

The term "PBMC" or "peripheral blood mononuclear cells" or "unfractionated PBMC", as used herein, refers to whole PBMC, i.e. to a population of white blood cells having a round nucleus, which has not been enriched for a given sub-population. Cord blood mononuclear cells are further included in this definition. Typically, the PBMC sample according to the invention has not been subjected to a selection step to contain only adherent PBMC (which consist essentially of >90% monocytes) or non-adherent PBMC (which contain T cells, B cells, natural killer (NK) cells, NK T cells and DC precursors). A PBMC sample according to the invention therefore contains lymphocytes (B cells, T cells, NK cells, NKT cells), monocytes, and precursors thereof. Typically, these cells can be extracted from whole blood using Ficoll, a hydrophilic polysaccharide that separates layers of blood, with the PBMC forming a cell ring under a layer of plasma. Additionally, PBMC can be extracted from whole blood using a hypotonic lysis buffer which will preferentially lyse red blood cells. Such procedures are known to the expert in the art.

sequence databases, the nucleic acid sequences corresponding to each of the gene of interest described herein may be retrieved by the one skilled in the art. For avoidance of doubt, each gene of the present invention is characterized in Table A with its access number available on www.ncbi.nlm.nih.gov/gene/:

TABLE A

Genes included in the IFN Score with corresponding locus, encoded protein and function

| Gene | Location | Protein | Function | Entrez ID |
|---|---|---|---|---|
| DDX58 | 9p21.1 | RIG-I | RNA Helicase, PRR for viral RNA | 23586 |
| OAS2 | 12q24.13 | 2'-5'-oligoadenylate synthetase 2 | 2-5A synthetase responsible for RNase L activation and degradation of viral RNA | 4939 |
| MX2 | 21q22.3 | Interferon-induced GTP-binding protein Mx2 | Anti-viral activity (HIV and SIV). May play a role in regulating nucleocytoplasmic transport and cell-cycle progression | 4600 |
| TRIM22 | 11p15.4 | Tripartite motif-containing 22 | Interferon-induced antiviral protein involved in cell innate immunity. The antiviral activity could in part be mediated by TRIM22-dependent ubiquitination of viral proteins | 10346 |
| GBP4 | 1p22.2 | Guanylate binding protein 4 | Binds GTP, GDP and GMP. Hydrolyzes GTP with GDP or GMP being reaction products | 115361 |
| CXCL10 | 4q21.1 | C-X-C motif chemokine 10 | Chemotactic for monocytes and T-lymphocytes. Binds to CXCR3. | 3627 |
| IFIT1 | 10q23.31 | IFN-induced protein with tetratricopeptide repeats 1 | Antiviral RNA-binding protein acting as a sensor of viral single-stranded RNAs and inhibiting expression of viral mRNA. | |
| IFIH1 | 2q24.2 | Melanoma Differentiation-Associated protein 5 | RIG-I-like receptor dsRNA helicase enzyme acting as a cytoplasmic sensor of viral RNA. Major role in sensing viral infection and in activation of antiviral responses. | 64135 |

In some embodiments, both the expression levels of OAS2 and MX2 are determined at step i).

In some embodiments, the expression level of at least one further gene is determined and compared to its corresponding predetermined value. In some embodiments, the gene for which the expression is further determined is selected from the group consisting of IFIT1, CXCL10, IFIH1, DDX58, TRIM22 and GBP4.

In some embodiments, the expression levels of 2, 3, 4, 5, 6, 7 or 8 genes are determined.

In some embodiments, the expression levels of OAS2, MX2, IFIT1, CXCL10, IFIH1, DDX58, TRIM22 and GBP4 are determined in the sample and compared to their corresponding predetermined reference value.

In a further aspect, the expression level of at least one gene selected from the group consisting of OAS2, MX2, IFIT1, CXCL10, IFIH1, DDX58, TRIM22, GBP4, DDX60, IFIT5, IFI44 and IRF1 are determined in the sample and compared to their corresponding predetermined reference value In some embodiments, the expression levels of 2, 3, 4, 5, 6, 7, 8, 9, 10, 11 or 12 genes are determined.

In the present specification, the name of each of the genes of interest refers to the official gene symbol of the corresponding gene, as found in internationally recognised gene sequences and protein sequences databases, in particular in the database from the HUGO Gene Nomenclature Committee, that is available notably at the following Internet address: www.gene.ucl.ac.uk/nomenclature/index.html. In the present specification, the name of each of the various biological markers of interest may also refer to the internationally recognised name of the corresponding gene, as found in the internationally recognised gene sequences and protein sequences databases ENTRE ID, Genbank, TrEMBL or ENSEMBL. Through these internationally recognised

TABLE B

Further genes included in the method of the invention with corresponding encoded protein and function

| Gene | Protein | Function | Entrez ID |
|---|---|---|---|
| DDX60 | DEXD/H-box helicase 60 | Positively regulates DDX58/RIG-I- and IFIH1/MDA5-dependent type I interferon and interferon inducible gene expression in response to viral infection. Binds ssRNA, dsRNA and dsDNA and can promote the binding of DDX58/RIG-I to dsRNA. | 55601 |
| IFIT5 | Interferon induced protein with tetratrico-peptide repeats 5 | Interferon-induced RNA-binding protein that specifically binds single-stranded RNA bearing a 5'-triphosphate group (PPP-RNA), thereby acting as a sensor of viral single-stranded RNAs. Single-stranded PPP-RNAs are specific from viruses, providing a molecular signature to distinguish between self and non-self mRNAs. | 24138 |
| IFI44 | Interferon induced protein 44 | This protein aggregates to form microtubular structures | 10561 |
| IRF1 | Interferon regulatory factor 1 | Serves as an activator of interferons alpha and beta transcription (required for double-stranded RNA induction of these genes in mouse). Also functions as a transcription activator of genes induced by interferons alpha, beta, and gamma. Plays also roles in regulating apoptosis and tumor-suppression | 3659 |

Determination of the expression level of a gene can be performed by a variety of techniques. Generally, the expression level as determined is a relative expression level. Typically, the determination comprises contacting the sample with selective reagents such as probes, primers or ligands, and thereby detecting the presence, or measuring the amount, of polypeptide or nucleic acids of interest originally in the sample. Contacting may be performed in any suitable device, such as a plate, microtiter dish, test tube, well, glass, column, and so forth. In some embodiments, the contacting is performed on a substrate coated with the reagent, such as a nucleic acid array or a specific ligand array. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as a nucleic acid hybrid or an antibody-antigen complex, to be formed between the reagent and the nucleic acids or polypeptides of the sample.

In some embodiments, the expression level may be determined by determining the quantity of mRNA. Methods for determining the quantity of mRNA are well known in the art. For example the nucleic acid contained in the sample is first extracted according to standard methods, for example using lytic enzymes or chemical solutions or extracted by nucleic-acid-binding resins following the manufacturer's instructions. The extracted mRNA is then detected by hybridization (e. g., Northern blot analysis) and/or amplification (e.g., RT-PCR). Typically quantitative or semi-quantitative RT-PCR is preferred. Real-time quantitative or semi-quantitative RT-PCR is particularly advantageous. Other methods of Amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization.

Typically, the nucleic acid probes include one or more labels, for example to permit detection of a target nucleic acid molecule using the disclosed probes. In various applications, such as in situ hybridization procedures, a nucleic acid probe includes a label (e.g., a detectable label). A "detectable label" is a molecule or material that can be used to produce a detectable signal that indicates the presence or concentration of the probe (particularly the bound or hybridized probe) in a sample. Thus, a labeled nucleic acid molecule provides an indicator of the presence or concentration of a target nucleic acid sequence (e.g., genomic target nucleic acid sequence) (to which the labeled uniquely specific nucleic acid molecule is bound or hybridized) in a sample. A label associated with one or more nucleic acid molecules (such as a probe generated by the disclosed methods) can be detected either directly or indirectly. A label can be detected by any known or yet to be discovered mechanism including absorption, emission and/or scattering of a photon (including radio frequency, microwave frequency, infrared frequency, visible frequency and ultraviolet frequency photons). Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected by antibody binding interactions, and paramagnetic and magnetic molecules or materials.

Particular examples of detectable labels include fluorescent molecules (or fluorochromes). Numerous fluorochromes are known to those of skill in the art, and can be selected, for example from Life Technologies (formerly Invitrogen), e.g., see, The Handbook—A Guide to Fluorescent Probes and Labeling Technologies). Examples of particular fluorophores that can be attached (for example, chemically conjugated) to a nucleic acid molecule (such as a uniquely specific binding region) are provided in U.S. Pat. No. 5,866,366 to Nazarenko et al., such as 4-acetamido-4'-isothiocyanatostilbene-2,2' disulfonic acid, acridine and derivatives such as acridine and acridine isothiocyanate, 5-(2'-aminoethyl) amino naphthalene-1-sulfonic acid (EDANS), 4-amino-N-[$^3$ vinylsulfonyl)phenyl]naphthalimide-3,5 disulfonate (Lucifer Yellow VS), N-(4-anilino-1-naphthyl)maleimide, antl1ranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diarninidino-2-phenylindole (DAPI); 5',5"dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulforlic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6dicllllorotriazin-2-yDarninofluorescein (DTAF), 2'7'dimethoxy-4'5'-dichloro-6-carboxyfluorescein (JOE), fluorescein, fluorescein isothiocyanate (FITC), and QFITC Q(RITC); 2',7'-difluorofluorescein (OREGON GREEN®); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives. Other suitable fluorophores include thiol-reactive europium chelates which emit at approximately 617 mn (Heyduk and Heyduk, Analyt. Biochem. 248:216-27, 1997; J. Biol. Chem. 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art can also be used, for example those available from Life Technologies (Invitrogen; Molecular Probes (Eugene, Oreg.)) and including the ALEXA FLUOR® series of dyes (for example, as described in U.S. Pat. Nos. 5,696,157, 6,130,101 and 6,716, 979), the BODIPY series of dyes (dipyrrometheneboron difluoride dyes, for example as described in U.S. Pat. Nos. 4,774,339, 5,187,288, 5,248,782, 5,274,113, 5,338,854, 5,451,663 and 5,433,896), Cascade Blue (an amine reactive derivative of the sulfonated pyrene described in U.S. Pat. No. 5,132,432) and Marina Blue (U.S. Pat. No. 5,830,912).

In addition to the fluorochromes described above, a fluorescent label can be a fluorescent nanoparticle, such as a semiconductor nanocrystal, e.g., a QUANTUM DOT™ (obtained, for example, from Life Technologies (Quantum-Dot Corp, Invitrogen Nanocrystal Technologies, Eugene, Oreg.); see also, U.S. Pat. Nos. 6,815,064; 6,682,596; and 6,649, 138). Semiconductor nanocrystals are microscopic particles having size-dependent optical and/or electrical properties. When semiconductor nanocrystals are illuminated with a primary energy source, a secondary emission of energy occurs of a frequency that corresponds to the handgap of the semiconductor material used in the semiconductor nanocrystal. This emission can be detected as colored light of a specific wavelength or fluorescence. Semiconductor nanocrystals with different spectral characteristics are described in e.g., U.S. Pat. No. 6,602,671. Semiconductor nanocrystals that can be coupled to a variety of biological molecules (including dNTPs and/or nucleic acids) or substrates by techniques described in, for example, Bruchez et al., Science 281:20132016, 1998; Chan et al., Science 281: 2016-2018, 1998; and U.S. Pat. No. 6,274,323. Formation of semiconductor nanocrystals of various compositions are disclosed in, e.g., U.S. Pat. Nos. 6,927,069; 6,914,256; 6,855,202; 6,709,929; 6,689,338; 6,500,622; 6,306,736; 6,225,198; 6,207,392; 6,114,038; 6,048,616; 5,990,479; 5,690,807; 5,571,018; 5,505,928; 5,262,357 and in U.S. Patent Puhlication No. 2003/0165951 as well as PCT Puhlication No. 99/26299 (puhlished May 27, 1999). Separate populations of semiconductor nanocrystals can he produced that are identifiable based on their different spectral characteristics. For example, semiconductor nanocrystals can he produced that emit light of different colors hased on their composition, size or size and composition. For example, quantum dots that emit light at different wavelengths based on size (565 mn, 655 mn, 705 mn, or 800 mn emission wavelengths), which are suitable as fluorescent labels in the probes disclosed herein are available from Life Technologies (Carlshad, Calif.).

Quantitative PCR is typically carried out in a thermal cycler with the capacity to illuminate each sample with a beam of light of a specified wavelength and detect the fluorescence emitted by the excited fluorophore. The thermal cycler is also able to rapidly heat and chill samples, thereby taking advantage of the physicochemical properties of the nucleic acids and thermal polymerase. The majority of the thermocyclers on the market now offer similar characteristics. Typically, thermocyclers involve a format of glass capillaries, plastics tubes, 96-well plates or 384-wells plates. The thermocylcer also involve a software analysis. In order to detect and measure the amount of amplicon (i.e. amplified target nucleic acid sequence) in the sample, a measurable signal has to be generated, which is proportional to the amount of amplified product.

In some embodiments, the expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the expression level, a sample from the patient, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (see e.g. the review by Hoheisel, Nature Reviews, Genetics, 2006, 7:200-210).

In some embodiments, the nCounter® Analysis system is used to detect intrinsic gene expression. The basis of the nCounter® Analysis system is the unique code assigned to each nucleic acid target to be assayed (International Patent Application Publication No. WO 08/124847, U.S. Pat. No. 8,415,102 and Geiss et al. Nature Biotechnology. 2008. 26(3): 317-325; the contents of which are each incorporated herein by reference in their entireties). The code is composed of an ordered series of colored fluorescent spots which create a unique barcode for each target to be assayed. A pair of probes is designed for each DNA or RNA target, a biotinylated capture probe and a reporter probe carrying the fluorescent barcode. This system is also referred to, herein, as the nanoreporter code system. Specific reporter and capture probes are synthesized for each target. The reporter probe can comprise at a least a first label attachment region to which are attached one or more label monomers that emit light constituting a first signal; at least a second label attachment region, which is non-over-lapping with the first label attachment region, to which are attached one or more label monomers that emit light constituting a second signal; and a first target-specific sequence. Preferably, each sequence specific reporter probe comprises a target specific sequence capable of hybridizing to no more than one gene and optionally comprises at least three, or at least four label attachment regions, said attachment regions comprising one or more label monomers that emit light, constituting at least a third signal, or at least a fourth signal, respectively. The capture probe can comprise a second target-specific sequence; and a first affinity tag. In some embodiments, the capture probe can also comprise one or more label attachment regions. Preferably, the first target-specific sequence of the reporter probe and the second target-specific sequence of the capture probe hybridize to different regions of the same gene to be detected. Reporter and capture probes are all pooled into a single hybridization mixture, the "probe library". The relative abundance of each target is measured in a single multiplexed hybridization reaction. The method comprises contacting the sample with a probe library, such that the presence of the target in the sample creates a probe pair-target complex. The complex is then purified. More specifically, the sample is combined with the probe library, and hybridization occurs in solution. After hybridization, the tripartite hybridized complexes (probe pairs and target) are purified in a two-step procedure using magnetic beads linked to oligonucleotides complementary to universal sequences present on the capture and reporter probes. This dual purification process allows the hybridization reaction to be driven to completion with a large excess of target-specific probes, as they are ultimately removed, and, thus, do not interfere with binding and imaging of the sample. All post hybridization steps are handled robotically on a custom liquid-handling robot (Prep Station, NanoString Technologies). Purified reactions are typically deposited by the Prep Station into individual flow cells of a sample cartridge, bound to a streptavidin-coated surface via the capture probe, electrophoresed to elongate the reporter probes, and immobilized. After processing, the sample cartridge is transferred to a fully automated imaging and data collection device (Digital Analyzer, NanoString Technologies). The expression level of a target is measured by imaging each sample and counting the number of times the code for that target is detected. For each sample, typically 600 fields-of-view (FOV) are imaged (1376×1024 pixels) representing approximately 10 mm2 of the binding surface. Typical imaging density is 100-1200 counted reporters per field of view depending on the degree of multiplexing, the amount of sample input, and overall target abundance. Data is output in simple spreadsheet format listing the number of counts per target, per sample. This system can be used along with nanoreporters. Additional disclosure regarding nanoreporters can be found in International Publication No. WO 07/076129 and WO07/076132, and US Patent Publication No. 2010/0015607 and 2010/0261026, the contents of which are incorporated herein in their entireties. Further, the term nucleic acid probes and nanoreporters can include the rationally designed (e.g. synthetic sequences) described in International Publication No. WO 2010/019826 and US Patent Publication No. 2010/0047924, incorporated herein by reference in its entirety.

Typically, the predetermined reference value is a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. For example, retrospective measurement of expression levels in properly banked historical patient samples may be used in establishing the predetermined reference value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after quantifying the expression level in a group of reference, one can use algorithmic analysis for the statistic treatment of the determined levels in samples to be tested, and thus obtain a classification standard having significance for sample classification. The full name of ROC curve is Receiver Operator Characteristic Curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is quite high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGN-ROC.FOR, MULTIREADER POWER.SAS, CREATE-ROC.SAS, GB STAT VI0.0 (Dynamic Microsystems, Inc. Silver Spring, Md., USA), etc.

In some embodiments, the predetermined reference value is determined by carrying out a method comprising the steps of a) providing a collection of samples from patients with decompensated alcoholic cirrhosis;

b) providing, for each sample provided at step a), information relating to the actual clinical outcome for the corresponding patient (i.e. the duration of the overall survival (OS));

c) providing a serial of arbitrary quantification values;

d) determining the expression level of the gene of interest for each sample contained in the collection provided at step a);

e) classifying said samples in two groups for one specific arbitrary quantification value provided at step c), respectively: (i) a first group comprising samples that exhibit a quantification value for level that is lower than the said arbitrary quantification value contained in the said serial of quantification values; (ii) a second group comprising samples that exhibit a quantification value for said level that is higher than the said arbitrary quantification value contained in the said serial of quantification values; whereby two groups of samples are obtained for the said specific quantification value, wherein the samples of each group are separately enumerated;

f) calculating the statistical significance between (i) the quantification value obtained at step e) and (ii) the actual clinical outcome of the subjects from which samples contained in the first and second groups defined at step f) derive;

g) reiterating steps f) and g) until every arbitrary quantification value provided at step d) is tested;

h) setting the said predetermined reference value as consisting of the arbitrary quantification value for which the highest statistical significance (most significant) has been calculated at step g).

For example the expression level has been assessed for 100 samples of 100 subjects. The 100 samples are ranked according to the expression level. Sample 1 has the highest density and sample 100 has the lowest density. A first grouping provides two subsets: on one side sample Nr 1 and on the other side the 99 other samples. The next grouping provides on one side samples 1 and 2 and on the other side the 98 remaining samples etc., until the last grouping: on one side samples 1 to 99 and on the other side sample Nr 100. According to the information relating to the actual clinical outcome for the corresponding patient, Kaplan Meier curves are prepared for each of the 99 groups of two subsets. Also for each of the 99 groups, the p value between both subsets was calculated. The predetermined reference value is then selected such as the discrimination based on the criterion of the minimum p value is the strongest. In other terms, the expression level corresponding to the boundary between both subsets for which the p value is minimum is considered as the predetermined reference value. It should be noted that the predetermined reference value is not necessarily the median value of expression levels. Thus in some embodiments, the predetermined reference value thus allows discrimination between a poor and a good prognosis with respect to survival time for a patient. Practically, high statistical significance values (e.g. low P values) are generally obtained for a range of successive arbitrary quantification values, and not only for a single arbitrary quantification value. Thus, in some embodiments, instead of using a definite predetermined reference value, a range of values is provided. Therefore, a minimal statistical significance value (minimal threshold of significance, e.g. maximal threshold P value) is arbitrarily set and a range of a plurality of arbitrary quantification values for which the statistical significance value calculated at step g) is higher (more significant, e.g. lower P value) are retained, so that a range of quantification values is provided. This range of quantification values includes a "cut-off" value as described above. For example, according to this specific embodiment of a "cut-off" value, the outcome can be determined by comparing the expression level with the range of values which are identified. In some embodiments, a cut-off value thus consists of a range of quantification values, e.g. centered on the quantification value for which the highest statistical significance value is found (e.g. generally the minimum p value which is found). For example, on a hypothetical scale of 1 to 10, if the ideal cut-off value (the value with the highest statistical significance) is 5, a suitable (exemplary) range may be from 4-6. For example, a patient may be assessed by comparing values obtained by determining the expression level of the gene of interest, where values greater than 5 reveal a poor prognosis and values less than 5 reveal a good prognosis. In a another embodiment, a patient may be assessed by comparing values obtained by measuring the expression level of the gene and comparing the values on a scale, where values above the range of 4-6 indicate a poor prognosis and values below the range of 4-6 indicate a good prognosis, with values falling within the range of 4-6 indicating an intermediate occurrence (or prognosis).

In some embodiments, when the expression levels of at least 2 genes are determined, a score which is a composite of said expression levels is calculated and compared to its corresponding predetermined reference value, wherein when the score is higher than the predetermined reference value it is concluded that the patient will have a short survival time and when the score is lower than the predetermined reference value, it is concluded that the patient will a long survival time. Typically the score is the IFN score as described in the EXAMPLE.

The method of the present invention is particularly suitable for determining whether a patient with decompensated alcoholic cirrhosis is eligible to liver transplantation. Accordingly a further object relates to a method of treating a patient with decompensated alcoholic cirrhosis comprising determining the survival time of the patient by the method of the present invention and performing liver transplantation when it is concluded that the patient will have a short survival time.

The invention will be further illustrated by the following FIGURES and examples. However, these examples and FIGURES should not be interpreted in any way as limiting the scope of the present invention.

EXAMPLES

Example 1

Patients and Methods
I—Patients

This protocol has been approved by the ethic committee (Comité de protection des personnes Ile de France III) and informed consent was obtained from every patients. 94 cirrhotic patients from the Liver Disease department of Beaujon Hospital (Assistance Publique—Hôpitaux de Paris, Clichy, 92110, France) were selected according the prerequisites of each experiment. As mentioned in the method section of part 1, patients enrolled in the study had severe decompensated biopsy-proven alcoholic cirrhosis. However, they were stable and did not have untreated or recently treated (less than 1 week) bacterial infection or gastrointestinal bleeding. Global characteristics of the patients are displayed in Table 1. Healthy subjects were selected among healthy caregivers. Fifteen to twenty milliliters of venous blood was sampled in 3 mL EDTA tubes (Becton Dickinson, France) from patients and healthy subjects. Clinical and biological data were collected and relevant prognostic scores calculated.

TABLE 1

Characteristics of patients with decompensated alcoholic cirrhosis enrolled during the second part of this work.

| Variable | n = 94 |
|---|---|
| Male | 77 (81.9) |
| Age (years) | 57.5 (50-61) |
| Child-Pugh Score | 11 (9-12) |
| MELD Score | 19.3 (15.6-23.8) |
| Serum Creatinine (µmol/L) | 84.2 (57.0-97.0) |
| Platelets (G/L) | 103.0 (65.2-140) |
| Leukocytes (G/L) | 6.9 (5-9.4) |
| Lymphocytes (G/L) | 1.1 (0.8-1.7) |
| Neutrophils (G/L) | 4.4 (2.9-6.6) |
| Monocytes (G/L) | 0.8 (0.5-1) |
| CRP | 13 (6-29) |
| Na (mmoL/L) | 135 (131-137) |
| CLIP SOFA score | 6 (4-7) |
| ACLF Grade | 0 (0-0) |
| Ascites | 79 (84.0) |
| Encephalopathy | 34 (36) |
| Antibiotic | 47 (50) |
| B-blockers | 39 (41.5) |
| Corticosteroids | 6 (6.6) |
| Acute alcoholic hepatitis | 24 (25.5) |

Results are expressed as number (percentage) or median (IQR)

II—PBMC and Monocyte Isolation and Culture, RNA Extraction, RT-qPCR

II-1. PBMC Isolation and Culture

PBMCs isolation and culture was performed as described in the corresponding patients and methods section of the part 1 of this work.

PBMCs from patients and healthy subjects were left unstimulated or stimulated for four hours with 1 µg/mL LPS (TLR4 agonist, *Escherichia coli* serotype 0111:B4, Sigma Aldrich St Louis, Mo., USA), 10 µg/mL Poly I:C (TLR3 agonist, Enzo Life Sciences, Farmingdale, N.Y., USA), 10 µg/mL poly I:C+lipofectamin (RLR agonist, Life Technologies, Carlsbad, Calif., USA) or 10 fold increasing concentrations of human IFN-β 1a (PBL Assay Science, Piscataway, N.J., USA) ranging from 1 UI/mL (5 pg/mL) to 1000 UI (5 µg/mL). In some experiments, PBMCs were stimulated with 1 µg/mL LPS (*Escherichia coli* serotype 0111:B4, Sigma Aldrich) for one hour only.

II-2. Monocyte Isolation and Culture

A reported corresponding patients and methods section of the part 1 of this work, after PBMC isolation, monocytes were separated from other immune cells using negative selection thanks to electromagnetic beads (Dynabeads®, Untouched human monocyte kit, Thermo Fischer scientific, Waltham, Mass., USA) following the manufacturer's protocol. Monocytes were cultured according the protocols described for PBMCs.

II-3. Cycloheximide

PBMC from patients were isolated, counted and cultured according to previously described protocol. Cells were pre-incubated or not for 15 minutes with Cycloheximide (CHX, 10 µg/mL, Sigma, St Louis, Mo., USA), a natural inhibitor of protein synthesis and then left untreated or stimulated with 1 µg/mL LPS for 4 hours. At the end of culture time, cells were harvested and lysed as hereafter described.

II-4. Brefeldin A

PBMC from patients were isolated, counted and cultured according to previously described protocol. Cells were incubated or not for 2 minutes with Brefeldin A (BRF, Sigma, St Louis, Mo., USA) an inhibitor of protein secretion and then left untreated or stimulated with 1 µg/mL LPS for 4 hours. At the end of culture time, cells were harvested and lysed as hereafter described.

II-5. IFN-α/β Receptor Chain 2 (IFNAR2) Blockade

PBMCs from patients and healthy subjects were isolated, counted and cultured according to previously described protocol with 1 µg/mL LPS. As described in previous studies [159], PBMCs were preincubated or not with with anti-human IFN-α/β receptor chain 2 monoclonal antibody (30 µg/mL, PBL Assay Science, Piscataway, N.J., USA) or control isotopic immunoglobulin fragment Fc (IgG2) and then left untreated or stimulated with 1 µg/mL LPS for 4 hours. At the end of the culture time, cells were harvested and lysed as hereafter described.

II-6. LPS Tolerance Experiments

PBMCs from patients and healthy subjects were stimulated one or two time(s) with LPS. They were stimulated or not a first time with 10 ng/mL LPS for 24 hours and then stimulated with 10 ng/mL LPS for 4 hours. Thus, on one hand, naïve PBMCs were only stimulated once with LPS for 4 hours after a 24 hours-culture period without stimulation and, on the other hand, tolerant PBMCs were also stimulated with LPS for four hours, but after previous a 24 hour low dose LPS stimulation.

II-7. RNA Isolation

See the corresponding paragraph in the materiel and methods section of the part 1 of this manuscript.

II-8. Reverse Transcription

Genomic DNA was eliminated using DNase I, RNase free kit (Fermentas Life Sciences, USA) following the manufacturer's protocol. One microgram of RNA was mixed with 1 µL of DNase and 1 µL of DNase I buffer in 10 µL volume and incubated during 30 minutes at 37° C. in a PCR thermocycler (Applied Biosystems 2720, Singapore). DNase activity was interrupted adding 1 µL of EDTA (50 mM) and incubating the mix during 10 minutes at 65° C. in the thermocycler. Reverse transcription was conducted using Thermo Fischer Scientific Verso cDNA Synthesis kit following the manufacturer's protocol (Thermo Fischer scientific, Waltham, Mass., USA). The previously obtained mix was completed with oligonucleotides oligo-DT primers, deoxynucleotides, buffer, enhancer and VERSO enzyme. The mix was incubated during 60 minutes at 42° C. Reverse transcriptase enzyme activity was stopped by warming at 95° C. and cDNA were stored à −20° C.

II-9. Real Time Quantitative PCR Analysis (RT-qPCR)

Quantitative PCR analysis was used to assess mRNA expression in immune cells. Specific Primers for studied genes were designed using Primer3web version 4.0. Percent PCR amplification efficiencies (E) were calculated for each primer as $E=(10-1/slope-1)\times100$, using the slope of the semi-log regression plot of Ct versus log input of cDNA (10-fold dilution series of five points). A threshold of 5% above or below 100% efficiency was applied (i.e. an efficiency between 1.9 and 2.1).[150] Then DNA solutions were diluted from 1/15 to 1/30 according the mRNA expression level. Ninety six well plates were used. Each wells was filled with 5 µL of diluted cDNA solution and a mixed solution containing 10 µL of SYBR Green I enzyme (ABgene, Thermo Scientific, Waltham, USA), 3 µL of distilled water and 2 µL of specific primers. Plates were sealed with plastic films and inserted in a Light Cycler 480 (Roche Diagnostics GmbH, Mannheim, Germany). Forty cycle thermocycling sequences were conducted. A melting curve was systematically run at the end the reaction to verify that the used primer pair produced a single product. Cycle Threshold (Ct) level was obtained for each gene tested. All analysis were conducted in duplicate. To favor technical reproducibility of the qPCR experiments, sample with standard deviation of the crossing point >0.3 from the mean Ct were excluded from analysis. Results were expressed as the N-fold differences in target gene expression relative to the GAPDH housekeeping gene expression in unstimulated PBMCs from healthy subjects. Results were determined as $2^{-\Delta Ct sample}$ where the ΔCt value of the sample was determined by substracting the average Ct value of the target gene from the average Ct value of the GAPDH gene. As described elsewhere, the obtained values of the samples were then normalized such that the median of the corresponding gene values in PBMCs from healthy subjects was 1.[160]

As previously described, the median fold change of 8 ISGs, when compared with the median of the combined healthy controls, was used to create an interferon score for each patient (Yao, Y., et al., Development of Potential Pharmacodynamic and Diagnostic Markers for Anti-IFN-alpha Monoclonal Antibody Trials in Systemic Lupus Erythematosus. Hum Genomics Proteomics, 2009. 2009.; Rice, G. I., et al., Assessment of interferon-related biomarkers in Aicardi-Goutieres syndrome associated with mutations in TREX1, RNASEH2A, RNASEH2B, RNASEH2C, SAMHD1, and ADAR: a case-control study. Lancet Neurol, 2013. 12(12): p. 1159-69.). Selected genes were the 7 most highly expressed interferon stimulated genes in LPS-stimulated «healthy» cells (i.e. IFIT1, CXCL10, MX2, IFIH1, DDX58, OAS2 and TRIM22) and GBP4 (as member of the physiopathologically important GBP family).

III—Statistical Analysis

Quantitative variables were when expressed as median (Interquartile range) and categorical variables as number (percentage). Comparisons between groups of quantitative variables were performed using Mann-Whitney test and Wilcoxon test appropriate. All tests were two-sided and used a significance level of 0.05. Data handling and analysis were performed with SPSS 22.0 (SPSS Inc., Chicago, Ill.) and GraphPad Prism version 6 for Mac OS X. Cumulative survival was calculated by Kaplan-Meier method. Patients who underwent liver transplantation were counted as censored. The potential relation of cytokine gene levels with the risk of death was analyzed by Cox regression univariate analysis. Each variable achieving a p value <0.05 was introduced into a Cox model with MELD score in order to determine whether these variables had a prognostic value independently of MELD score, as previously reported.

Results

I—LPS-Induced Expression of Genes Identified as ISGs by Interferome Database is Defective in PBMCs from Patients with Decompensated Alcoholic Cirrhosis Our expression microarrays revealed a core of 444 genes upregulated in "healthy" PBMCs but either non-regulated or downregulated in cirrhotic PBMCs belonging to the "defense response to virus" GO BP. Interestingly, quiering the interferome public database (interferome.its.monash.edu.au), we found that 174 of these genes were classified as ISGs among which, 168 were type 1 IFN-stimulated genes. Moreover, five other genes (IDO1, LAG3, OAS3, RSAD2 and USP18) classified as ISGs by interferome were induced by LPS both in "healthy" and cirrhotic PBMCs but their expression was more than two fold higher in "healthy" than in cirrhotic cells. Finally, one gene was down regulated by LPS in "cirrhotic" PBMCs whereas it was upregulated by LPS in "healthy PBMCs".

Next, we selected a set of 46 type-1 ISGs according to their functions and we measured, using RT-qPCR, the relative steady-state levels of mRNA from each gene in PBMCs stimulated with LPS, from an independent cohort of 33 patients with decompensated alcoholic cirrhosis and 17 healthy subjects. As a control, we also measured in PBMCs from the same patients under the same conditions the expression of 6 cytokine genes (IL10, IL12B, IL6, IL1B, IL8, and TNF) and 4 chemokine genes (CXCL1, CXCL2, CXCL3, CXCL5).

LPS induced all the 46 genes in both groups. However, the LPS-induced level of expression of 70% (32 over the 46 studied genes) of ISGs was significantly lower in "cirrhotic" PBMCs than in "healthy" PBMCs. Using western blotting, we confirmed this defect at the protein level. Indeed, we showed a lower expression of OAS2 (encoded by the ISG OAS2) protein levels in LPS-stimulated cirrhotic PBMCs, as compared to LPS-stimulated "healthy PBMCs.

Taken together, our results show, in PBMCs from patients with decompensated alcoholic cirrhosis, a defective LPS-induced expression of a large group of genes identified as type 1 IFN ISGs by interferome. This defective induction of ISGs in cirrhotic PBMCs was not due to an increased cellular death. Indeed, we quantified cell lysis and cell death by measuring lactate deshydrogenase (LDH) in supernatant from 4 h-LPS stimulated healthy (n=14) and cirrhotic (n=14) PBMCs using a colorimetric assay. We found a very low mean percentage of cytotoxicity that did not differ between healthy and cirrhotic cells (0.6% vs 1.1%, p=0.51). Furthermore, we found several cytokine and chemokine genes such TNF (encoding TNF-α), CXCL2, CXCL3 and CXCL5 (encoding ENA-78) with significantly higher LPS-induced expression in cirrhotic PBMCs. Finally, we found the similar defect of ISG expression after a one hour LPS stimulation.

II—Verification of the True ISG Status of the Genes

Functions of each gene were analyzed and, for practical reasons, a "restricted" set of 21 genes of interest identified as ISGs by interferome database and whose expression was altered in LPS-stimulated cirrhotic PBMCs was selected for experiments performed thereafter. We verified the "bona-fide" ISG status of each gene of interest using two approaches. First, we wondered if type I-IFN receptor (IFNAR) blocking would result in an inhibition of the induction of these genes by LPS. Thus, PBMCs from five patients with decompensated alcoholic cirrhosis were pre-incubated, or not, with a type I-IFN-α/β receptor chain 2 (IFNAR2) antagonist (30 µg/mL) for 15 minutes before being stimulated with LPS. We found that preincubation of cirrhotic cells with IFNAR2 antagonist abolished LPS-induced expression of 19 genes (95%), whereas incubation with the isotype control antibody did not. This inhibitory effect was specific for ISG as far as LPS-induced expression of genes encoding cytokines not known to belong to ISGs was not altered by preincubation with IFNAR2. Furthermore, IFNAR antibody had the same effect on ISG induction in LPS stimulated "healthy" PBMCs.

Secondly, we wondered if an IFN-β-stimulation would result in an induction of these genes. Thus, PBMCs from eight patients with decompensated alcoholic cirrhosis were stimulated with 10 UI/mL IFN-β. 18 of the 19 genes whose induction by LPS was sensitive to IFNAR antagonist were also induced by a 10 UI/mL-IFN-β stimulation. Thus, altogether, we found that among our restricted set of 21 genes of interest identified as ISGs by interferome public database, 18 (86%) were "bona-fide" ISGs in PBMCs from patients with decompensated alcoholic cirrhosis.

III—Construction of an ISG Signature Named IFN Score

As previously performed (Yao, Y., et al., Development of Potential Pharmacodynamic and Diagnostic Markers for Anti-IFN-alpha Monoclonal Antibody Trials in Systemic Lupus Erythematosus. Hum Genomics Proteomics, 2009. 2009.; Rice, G. I., et al., Assessment of interferon-related biomarkers in Aicardi-Goutieres syndrome associated with mutations in TREX1, RNASEH2A, RNASEH2B, RNASEH2C, SAMHD1, and ADAR: a case-control study. Lancet Neurol, 2013. 12(12): p. 1159-69.) we developed an ISG signature that was named IFN score to quantify the magnitude of the global downregulation of ISGs in PBMCs from patients with cirrhosis. Briefly, the IFN score was calculated for each patient and healthy subject as the median fold change of 8 ISGs normalized with the median of the combined healthy controls. The 7 most highly expressed ISGs (among the 18 bona fide ISGs identified above) in LPS-stimulated "healthy" cells (i.e. IFIT1, CXCL10, MX2, IFIH1, DDX58, OAS2 and TRIM22) were used in IFN score. In order to include a member of the physiopathologically important GBP family, we also selected GBP4, the most highly LPS-induced member of GBP family. Thus 8 ISGs were included in the IFN score. Their name, corresponding locus, encoded protein and functions are displayed in Table A.

Calculation the IFN score in LPS-stimulated PBMCs from previously mentioned decompensated cirrhotic patients and healthy subjects allowed us to confirmed the global defective induction of ISGs in immune cells from patients. It is important to note that IFN score values did not correlate with leukocyte, monocyte or lymphocyte counts and antibiotic or beta-blocker treatment of patients.

IV—Defects in Basal and LPS-Induced ISG Expression are Linked to the Severity of Cirrhosis As in patients with cirrhosis, alterations of innate immune response and bacterial translocation are closely linked to the severity of cirrhosis, we investigated unstimulated and LPS stimulated ISG expression in PBMCs from patients with increasing severity of cirrhosis as reflected by Child-Pugh score. 8 patients with Child-Pugh grade A, 20 with Child-Pugh grade B and 45 with Child-Pugh grade C cirrhosis were enrolled (Table 2).

TABLE 2

Characteristics of enrolled Child-Pugh A,
Child-Pugh B, and Child-Pugh C patients.

|  | Child Pugh A | Child Pugh B | Child-Pugh C |
|---|---|---|---|
| Number of patients, n | 7 | 20 | 28 |
| Sex (M/F) | 6 (0.85) | 17 (0.8) | 23 (82) |
| Age, yr | 59.5 (53-66) | 57 (51-60) | 59 (53-63) |
| Child-Pugh Score | 5 (5-5.2) | 8.5 (8-9) | 12 (11-13) |
| MELD | 8.9 (8-10) | 13 (10-16) | 21.2 (18-27) |
| Serum creatinine (μmol/L) | 68.5 (66-71) | 74.5 (67-97) | 67 (57-88) |
| Platelets (G/L) | 124 (81-147) | 113 (85-155) | 96 (56-120) |
| Leukocytes (G/L) | 5.2 (3.5-5.8) | 6 (4.4-7.7) | 7.3 (4.8-10.1) |
| Lymphocytes (G/L) | 1.16 (0.8-1.6) | 1.07 (0.8-1.5) | 1.03 (0.7-1.6) |
| Monocytes (G/L) | 0.39 (0.3-0.5) | 0.69 (0.5-0.9) | 0.78 (0.5-1.1) |
| CRP (mg/L) | 2.5 (2-4) | 11 (5-15) | 16 (6-30) |
| Na (mmol/L) | 138 (135-138) | 135 (131-137) | 134 (130-137) |
| CLIP SOFA score | 1.5 (1-2) | 3 (2.7-4) | 7 (5-8) |
| ACLF Grade | 0 (0) | 0 (0-0) | 0 (0-1) |
| Ascites, n (%) | 0 (0) | 15 (75) | 24 (87) |
| Encephalopathy | 0 (0) | 2 (10) | 13 (45) |
| Antibiotics, n (%) | 0 (0) | 5 (25) | 15 (55) |
| β-blocker, n (%) | 2 (28) | 5 (25) | 10 (37) |
| Corticosteroids, n (%) | 0 (0) | 0 (0) | 3 (11) |
| Histological alcoholic hepatitis, n (%) | 0 (0) | 2 (10) | 9 (33) |

As shown by lower IFN score values, we found that the defect in ISG expression of both unstimulated and LPS-stimulated immune cells significantly worsen with the severity of cirrhosis. Whereas, IFN score did not statistically differ between Child A patients and healthy subjects, it was significantly lower in Child-Pugh B and Child-Pugh C patients as compared to Child A ones. Thus, the lower ISG response seems to be restricted to the more severe cirrhotic patients.

V—Impact of ISG Expression on Patient Prognosis

Figure 1:
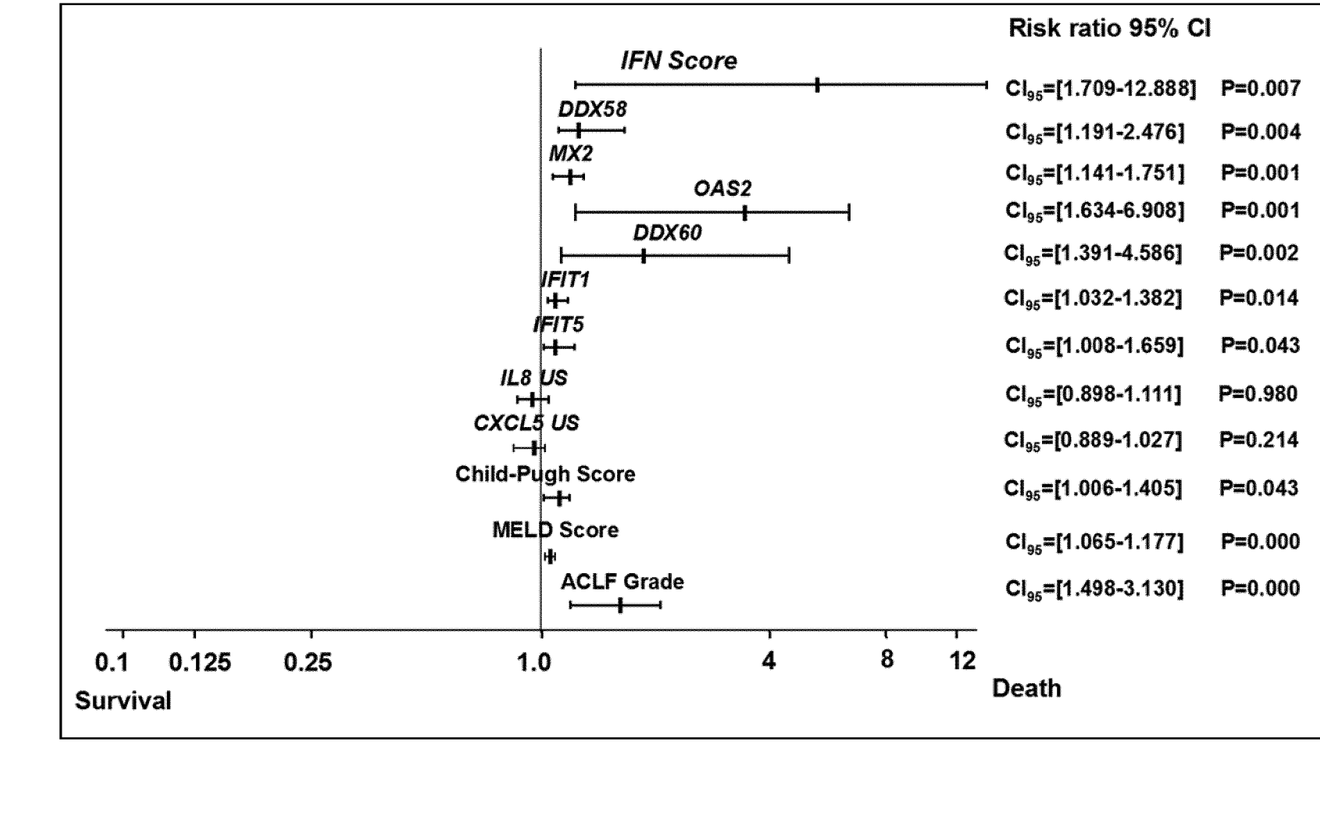
FIG. 1. Forrest plot showing the prognostic value of 6 ISGs, our IFN score, 2 cytokine genes and 3 well-known prognostic scores used in patients with cirrhosis in univariate analysis. Ex vivo RT-qPCR experiments were performed in PBMCs from 42-56 patients; however, results of relative mRNA expression were not obtained in some experiments due to inefficient annealing of primers and patients who underwent liver transplantation were counted as censored. The potential relation of cytokine gene levels to the risk of death (counted as event) was analyzed by Cox regression univariate analysis.

Finally, we aimed at demonstrating the paramount importance of the ISG system and its regulation in patients with cirrhosis by investigating the impact of its lower activation on patient outcome, we prospectively monitored survival of patients in whom PBMC ISG expression was measured. 40 patients (40%) died during a median (IQR) follow-up of 6.55 (1.32-12.60) months. Using cox model, we found that, in unstimulated cells, the value of our IFN score and the expression of six out of the 18 true ISGs of interest were associated with patient outcome in univariate analysis (FIG. 1). Interestingly, the lower the IFN score value and the ISG expression were, the better the outcome. These findings are consistent with the hypothesis of a beneficial downregulation of ISG expression in patients with severe cirrhosis to avoid immunopathology. The major importance of the ISG system was emphasized by the fact that the odds ratio of IFN score value in unstimulated cells for predicting death was much more higher than those of usual cirrhotic patients prognostic scores such as MELD score, Child-Pugh score, CLIF-SOFA score and ACLF grade (FIG. 1). Furthermore, unlike ISGs, unstimulated expression of usual cytokine gene did not have any prognostic value (FIG. 1). Expression of ISGs and cytokine genes after LPS stimulation were not associated with outcome. In multivariate analysis, high basal IFN score value remained a risk factor of death independently of MELD score, CLIF SOFA score and CRP level (Table 3). Interestingly, half of these deaths were due to septic shock and 86% due to multiple organ failure (Table 4). At the gene level, high basal MX2 and OAS2 expressions also predicted death independently of MELD score and CLIF SOFA. Interestingly, in our cohort IFN score had the best death predicting ability for patients with MELD score lower than 19, the median MELD score of our cohort. Thus, our IFN score may allow an early detection of patients with stable decompensated cirrhosis who particularly are at risk of death in the next future. Indeed, this subgroup of patients may derive the maximum benefit from liver transplantation.

TABLE 3

Prognostic value of the basal IFN score, MX2 and OAS2 expressions and of usual cirrhotic patient prognostic scores (MELD score and CLIF SOFA score). Ex vivo RT-qPCR experiments were performed in PBMCs from 42-56 patients. However, results of relative mRNA expression were not obtained in some experiments due to inefficient annealing of primers and patients who underwent liver transplantation were counted as censored. For bivariate analyses: we fitted 5 Cox models including MELD score with each variable achieving a p < 0.05 successively, in order to determine if these variables had a prognostic value independently of usual cirrhotic patient prognostic scores (MELD score, CLIF SOFA score and CRP levels).

|  | Number of events | Total number of patients | Risk ratio | 95.0% CI for risk ratio Lower | 95.0% CI for risk ratio Upper | P value |
|---|---|---|---|---|---|---|
| First model | 14 | 43 |  |  |  |  |
| IFN Score basal |  |  | 3.583 | 1.177 | 10.905 | .025 |
| MELD score |  |  | 1.071 | .993 | 1.155 | .074 |

TABLE 3-continued

Prognostic value of the basal IFN score, MX2 and OAS2 expressions and of usual cirrhotic patient prognostic scores (MELD score and CLIF SOFA score). Ex vivo RT-qPCR experiments were performed in PBMCs from 42-56 patients. However, results of relative mRNA expression were not obtained in some experiments due to inefficient annealing of primers and patients who underwent liver transplantation were counted as censored. For bivariate analyses: we fitted 5 Cox models including MELD score with each variable achieving a $p < 0.05$ successively, in order to determine if these variables had a prognostic value independently of usual cirrhotic patient prognostic scores (MELD score, CLIF SOFA score and CRP levels).

|  | Number of events | Total number of patients | Risk ratio | 95.0% CI for risk ratio | | P value |
|---|---|---|---|---|---|---|
|  |  |  |  | Lower | Upper |  |
| Second model | 14 | 43 |  |  |  |  |
| IFN Score basal |  |  | 3.958 | 1.358 | 11.533 | .012 |
| CLIF SOFA score |  |  | 1.126 | .904 | 1.403 | .288 |
| Third model | 13 | 42 |  |  |  |  |
| IFN Score basal |  |  | 4.072 |  |  | .007 |
| CRP |  |  | 1.007 |  |  | .454 |
| Fourth model | 21 | 56 |  |  |  |  |
| MX2 basal expression |  |  | 1.346 | 1.077 | 1.681 | .009 |
| MELD score |  |  | 1.091 | 1.020 | 1.167 | .011 |
| Fifth model | 21 | 56 |  |  |  |  |
| MX2 basal expression |  |  | 1.416 | 1.144 | 1.752 | .001 |
| CLIF SOFA score |  |  | 1.301 | 1.063 | 1.591 | .010 |
| Sixth model | 20 | 55 |  |  |  |  |
| OAS2 basal expression |  |  | 2.492 | 1.053 | 5.901 | .038 |
| MELD score |  |  | 1.060 | .984 | 1.141 | .122 |
| Seventh model | 20 | 55 |  |  |  |  |
| OAS2 basal expression |  |  | 2.754 | 1.235 | 6.140 | .013 |
| CLIF SOFA score |  |  | 1.153 | .930 | 1.429 | .195 |

TABLE 4

Causes of death (n = 14) in the cohort of patients in whom IFN score was measured (n = 43)

| Cause of death | n (%) |
|---|---|
| Septic shock | 7 (50) |
| MOF without aetiology | 3 (22) |
| MOF following hemorrhagic shock | 2 (14) |
| Hepatorenal syndrome | 1 (7) |
| Unknown | 1 (7) |

Example 2

Baseline ISG Expression is Related to Outcome in Cirrhosis

The inventors prospectively followed-up a cohort of patients after measurement of PBMC ISG expression at enrollment. Forty-one patients died during a median follow-up of 6.55 (1.32-12.60) months. A univariate Cox model showed that higher mortality was significantly associated with a higher model of end-stage liver disease (MELD) score, a higher IFN score in unstimulated cells, and higher expressions of DDX58, MX2, OAS2, DDX60, IFI44, IFIT1, IFIT5 and IRF1 in unstimulated cells (FIG. 1; Table 5). Unlike ISGs, cytokine gene expression (including the ISG CXCL10) did not significantly predict death in unstimulated cells (FIG. 1; Table 5). Only one (IFI35) of the genes measured in LPS-stimulated cells significantly predicted death (Table 5). Bivariate analysis including the baseline IFN and MELD scores only showed the former to be significantly predictive of death (Table 6). These results are mainly explained by the intrinsic prognostic value of higher baseline MX2, OAS2, and DDX58. Finally, higher baseline expressions of IFI44 and DDX60 were significant predictors of death, independent of the MELD score (Table 6).

TABLE 5

Prognostic value of the MELD score and ex vivo ISG and cytokine gene expression in unstimulated and LPS-stimulated PBMCs from patients with cirrhosis, Related to FIG. 1. Genes highlighted had significant prognostic value ($p < 0.05$).

| Variables in the Equation | Total number of patients | Number of events | Risk ratio | 95.0% CI for risk ratio | | p value |
|---|---|---|---|---|---|---|
| Prognostic scores | | | | | | |
| MELD score | 98 | 41 | 1.120 | 1.065 | 1.177 | <0.001 |
| Gene expression in unstimulated cells | | | | | | |
| Interferon-stimulated genes | | | | | | |
| AIM2 | 15 | 8 | .965 | .162 | 5.746 | .969 |
| BST2 | 18 | 10 | 1.199 | .311 | 4.623 | .792 |
| CXCL10 | 60 | 20 | 1.045 | .959 | 1.139 | .316 |
| CXCL11 | 13 | 8 | 1.285 | .272 | 6.065 | .751 |
| DDX58 | 55 | 21 | 1.717 | 1.191 | 2.476 | .004 |
| DDX60 | 46 | 16 | 2.526 | 1.391 | 4.586 | .002 |
| DHX58 | 49 | 18 | 1.209 | .729 | 2.005 | .461 |
| EIF2AK2 | 18 | 9 | 1.128 | .690 | 1.845 | .631 |
| GBP1 | 17 | 9 | 1.194 | .521 | 2.738 | .676 |
| GBP2 | 16 | 9 | .468 | .087 | 2.526 | .378 |
| GBP3 | 47 | 17 | 1.330 | .880 | 2.011 | .176 |
| GBP4 | 53 | 19 | 1.217 | .723 | 2.047 | .459 |
| GBP5 | 16 | 9 | .367 | .095 | 1.416 | .146 |
| HERC5 | 18 | 10 | 1.448 | .707 | 2.966 | .312 |
| IDO1 | 17 | 9 | 1.073 | .957 | 1.203 | .228 |

TABLE 5-continued

Prognostic value of the MELD score and ex vivo ISG and cytokine gene expression in unstimulated and LPS-stimulated PBMCs from patients with cirrhosis, Related to FIG. 1. Genes highlighted had significant prognostic value (p < 0.05).

| Variables in the Equation | Total number of patients | Number of events | Risk ratio | 95.0% CI for risk ratio | | p value |
|---|---|---|---|---|---|---|
| IFI16 | 16 | 8 | .527 | .054 | 5.099 | .580 |
| IFI35 | 54 | 21 | 1.067 | .905 | 1.259 | .440 |
| IFI44 | 17 | 9 | 1.711 | 1.091 | 2.683 | .019 |
| IFIH1 | 54 | 20 | 1.551 | .982 | 2.449 | .060 |
| IFIT1 | 50 | 18 | 1.168 | 1.032 | 1.322 | .014 |
| IFIT2 | 16 | 9 | 1.339 | .964 | 1.862 | .082 |
| IFIT3 | 49 | 18 | 1.016 | .987 | 1.047 | .282 |
| IFIT5 | 40 | 14 | 1.293 | 1.008 | 1.659 | .043 |
| IFITM3 | 18 | 10 | 1.084 | .903 | 1.300 | .387 |
| IFNB1 | 37 | 17 | 1.157 | .907 | 1.476 | .241 |
| IFNG | 41 | 13 | .870 | .584 | 1.295 | .493 |
| IRF1 | 56 | 22 | 1.699 | 1.049 | 2.752 | .031 |
| ISG20 | 17 | 9 | .624 | .200 | 1.950 | .418 |
| MB21D1 | 48 | 20 | 1.611 | .761 | 3.411 | .213 |
| MCOLN2 | 15 | 8 | 1.002 | .446 | 2.251 | .996 |
| MOV10 | 54 | 19 | 1.768 | .867 | 3.605 | .117 |
| MX1 | 15 | 10 | 1.176 | .767 | 1.801 | .457 |
| MX2 | 56 | 21 | 1.416 | 1.151 | 1.741 | .001 |
| OAS1 | 16 | 9 | 1.914 | .799 | 4.585 | .145 |
| OAS2 | 55 | 20 | 3.359 | 1.634 | 6.908 | .001 |
| PNPT1 | 17 | 9 | 1.048 | .262 | 4.199 | .947 |
| RSAD2 | 17 | 10 | 1.108 | .920 | 1.335 | .280 |
| SMCHD1 | 18 | 10 | .904 | .495 | 1.651 | .742 |
| TLR3 | 49 | 19 | 1.341 | .578 | 3.115 | .495 |
| TLR7 | 52 | 20 | 1.449 | .479 | 4.384 | .511 |
| TREX1 | 50 | 19 | .968 | .597 | 1.570 | .895 |
| TRIM14 | 55 | 21 | 1.930 | .982 | 3.793 | .057 |
| TRIM21 | 47 | 15 | 2.156 | .775 | 5.995 | .141 |
| TRIM22 | 48 | 18 | 1.180 | .579 | 2.403 | .649 |
| TRIM25 | 16 | 9 | .704 | .174 | 2.848 | .623 |
| TRIM5 | 16 | 9 | 1.193 | .772 | 1.843 | .426 |
| USP18 | 13 | 8 | .901 | .407 | 1.995 | .798 |
| XRN1 | 18 | 10 | 1.211 | .158 | 9.249 | .854 |
| ZBP1 | 52 | 19 | 1.548 | .937 | 2.558 | .088 |
| Cytokine genes | | | | | | |
| IL10 | 81 | 34 | 1.152 | .643 | 2.063 | .634 |
| IL6 | 52 | 20 | .989 | .966 | 1.012 | .353 |
| IL1B | 70 | 28 | 1.020 | .978 | 1.063 | .355 |
| IL8 | 47 | 22 | .999 | .898 | 1.111 | .980 |
| CXCL1 | 50 | 22 | 1.014 | .967 | 1.063 | .579 |
| CXCL2 | 52 | 23 | .989 | .925 | 1.057 | .746 |
| CXCL3 | 51 | 22 | .977 | .931 | 1.025 | .337 |
| CXCL5 | 48 | 21 | .955 | .889 | 1.027 | .214 |
| TNF | 37 | 17 | .362 | .103 | 1.275 | .114 |
| Gene expression in LPS-stimulated cells Interferon-stimulated genes | | | | | | |
| AIM2 | 7 | 6 | 1.562 | .616 | 3.959 | .348 |
| BST2 | 10 | 7 | 1.823 | .551 | 6.031 | .325 |
| CXCL10 | 40 | 12 | .991 | .945 | 1.039 | .704 |
| CXCL11 | 8 | 5 | .993 | .811 | 1.216 | .948 |
| DDX58 | 33 | 12 | 1.004 | .958 | 1.052 | .883 |
| DDX60 | 28 | 10 | 1.030 | .866 | 1.225 | .739 |
| DHX58 | 31 | 11 | .970 | .796 | 1.182 | .763 |
| EIF2AK2 | 15 | 9 | .779 | .581 | 1.046 | .097 |
| GBP1 | 10 | 7 | 1.047 | .902 | 1.215 | .546 |
| GBP2 | 10 | 7 | 1.402 | .734 | 2.677 | .307 |
| GBP3 | 28 | 11 | .993 | .874 | 1.128 | .915 |
| GBP4 | 33 | 12 | 1.009 | .891 | 1.141 | .891 |
| GBP5 | 10 | 7 | 1.115 | .913 | 1.363 | .286 |
| HERC5 | 10 | 7 | 1.019 | .781 | 1.329 | .891 |
| IDO1 | 10 | 7 | .989 | .944 | 1.036 | .650 |
| IFI16 | 17 | 9 | 1.386 | .615 | 3.126 | .431 |
| IFI35 | 26 | 10 | 1.313 | 1.007 | 1.711 | .044 |
| IFI44 | 19 | 10 | .994 | .937 | 1.053 | .830 |
| IFIH1 | 33 | 12 | 1.005 | .958 | 1.055 | .827 |
| IFIT1 | 31 | 12 | 1.021 | .950 | 1.097 | .573 |
| IFIT2 | 9 | 6 | 1.033 | .847 | 1.261 | .748 |
| IFIT3 | 31 | 10 | 1.058 | .930 | 1.203 | .392 |
| IFIT5 | 19 | 7 | 1.149 | .648 | 2.038 | .635 |
| IFITM3 | 9 | 6 | 1.032 | .781 | 1.364 | .825 |
| IFNB1 | 23 | 8 | .991 | .920 | 1.068 | .812 |
| IFNG | 28 | 8 | 1.001 | .998 | 1.003 | .716 |
| IRF1 | 32 | 12 | 1.186 | .851 | 1.652 | .315 |
| ISG20 | 10 | 7 | 1.059 | .724 | 1.550 | .766 |
| MB21D1 | 31 | 12 | 1.068 | .689 | 1.658 | .768 |
| MCOLN2 | 10 | 7 | 1.193 | .937 | 1.520 | .153 |
| MOV10 | 33 | 12 | 1.148 | .936 | 1.408 | .186 |
| MX1 | 10 | 7 | 1.062 | .832 | 1.354 | .631 |
| MX2 | 33 | 12 | 1.046 | .978 | 1.118 | .189 |
| OAS1 | 9 | 6 | 1.249 | .761 | 2.050 | .379 |
| OAS2 | 33 | 12 | 1.075 | .941 | 1.228 | .289 |
| PNPT1 | 19 | 10 | 1.529 | .490 | 4.764 | .464 |
| RSAD2 | 9 | 6 | .977 | .803 | 1.188 | .812 |
| SMCHD1 | 9 | 6 | 1.632 | .780 | 3.413 | .193 |
| TLR3 | 26 | 10 | .782 | .457 | 1.338 | .370 |
| TLR7 | 31 | 12 | .962 | .591 | 1.567 | .876 |
| TREX1 | 28 | 10 | 1.078 | .754 | 1.541 | .680 |
| TRIM14 | 32 | 12 | 1.079 | .788 | 1.477 | .637 |
| TRIM21 | 31 | 10 | 1.324 | .913 | 1.918 | .139 |
| TRIM22 | 33 | 12 | .989 | .854 | 1.145 | .881 |
| TRIM25 | 8 | 6 | .688 | .273 | 1.735 | .428 |
| TRIM5 | 10 | 7 | 1.256 | .688 | 2.294 | .458 |
| USP18 | 10 | 7 | 1.173 | .818 | 1.681 | .386 |
| XRN1 | 10 | 7 | 1.241 | .449 | 3.425 | .677 |
| ZBP1 | 31 | 12 | 1.091 | .984 | 1.210 | .098 |
| Cytokine genes | | | | | | |
| IL10 | 56 | 24 | .982 | .939 | 1.026 | .414 |
| IL6 | 50 | 19 | 1.000 | 1.000 | 1.000 | .968 |
| IL1B | 54 | 21 | .996 | .984 | 1.008 | .491 |
| IL8 | 50 | 23 | 1.002 | .997 | 1.007 | .440 |
| CXCL1 | 46 | 21 | 1.002 | .998 | 1.005 | .360 |
| CXCL2 | 45 | 20 | 1.000 | .999 | 1.002 | .539 |
| CXCL3 | 48 | 22 | 1.001 | .998 | 1.005 | .425 |
| CXCL5 | 46 | 22 | .987 | .966 | 1.009 | .244 |
| TNF | 41 | 20 | 1.002 | .993 | 1.010 | .738 |

TABLE 6

Baseline ISG expression is related to patients' outcome. Results of analysis using a bivariate model.

| | Number of events | Total number of patients | Risk ratio | 95.0% CI for risk ratio | | P value |
|---|---|---|---|---|---|---|
| | | | | Lower | Upper | |
| First model | 14 | 43 | | | | |
| IFN Score basal | | | 3.583 | 1.177 | 10.905 | .025 |
| MELD score | | | 1.071 | .993 | 1.155 | .074 |

TABLE 6-continued

Baseline ISG expression is related to patients' outcome. Results of analysis using a bivariate model.

| | Number of events | Total number of patients | Risk ratio | 95.0% CI for risk ratio | | P value |
|---|---|---|---|---|---|---|
| | | | | Lower | Upper | |
| Second model | 21 | 56 | | | | |
| MX2 basal expression | | | 1.346 | 1.077 | 1.681 | .009 |
| MELD score | | | 1.091 | 1.020 | 1.167 | .011 |
| Third model | 20 | 55 | | | | |
| OAS2 basal expression | | | 2.492 | 1.053 | 5.901 | .038 |
| MELD score | | | 1.060 | .984 | 1.141 | .122 |
| Fourth model | 10 | 26 | | | | |
| IFI35 basal expression | | | 1.393 | 1.043 | 1.861 | .025 |
| MELD score | | | 1.178 | 1.026 | 1.351 | .020 |
| Fifth model | 9 | 17 | | | | |
| IFI44 basal expression | | | 1.635 | 1.017 | 2.627 | .042 |
| MELD score | | | 1.032 | .936 | 1.136 | .529 |

REFERENCES

Throughout this application, various references describe the state of the art to which this invention pertains. The disclosures of these references are hereby incorporated by reference into the present disclosure.

The invention claimed is:

1. A method of treating a patient with decompensated alcoholic cirrhosis having a decreased survival time comprising
    i) determining the mRNA expression level of OAS2 or MX2 in a sample of peripheral blood mononuclear cells obtained from the patient,
    ii) comparing the level determined at step i) with the mRNA expression level of OAS2 or MX2 in healthy subjects,
    iii) determining that the patient will have a decreased survival time when the level determined at step i) is higher than the mRNA expression level of OAS2 or MX2 in healthy subjects, and
    iv) performing liver transplantation on the patient determined to have a decreased survival time.

2. The method of claim 1 wherein the expression levels of OAS2 and MX2 are determined at step i).

3. The method of claim 1 wherein the expression level of at least one further gene is determined and compared to its corresponding expression level in healthy subjects.

4. The method of claim 3 wherein the gene for which the expression is further determined is selected from the group consisting of IFIT1, CXCL10, IFIH1, DDX58, TRIM22 and GBP4.

5. The method of claim 4 wherein the expression levels of 2, 3, 4, 5, 6, 7 or 8 genes are determined.

6. The method of claim 4 wherein the expression levels of OAS2, MX2, IFIT1, CXCL10, IFIH1, DDX58, TRIM22 and GBP4 are determined in the sample.

7. The method of claim 1 wherein the expression level of the gene is determined by RT-PCR.

* * * * *